US005712114A

United States Patent [19]
Mankovich et al.

[11] Patent Number: 5,712,114
[45] Date of Patent: Jan. 27, 1998

[54] COMPOSITIONS FOR EXPRESSION OF PROTEINS IN HOST CELLS USING A PREPROCOLLAGEN SIGNAL SEQUENCE

[75] Inventors: John A. Mankovich, Andover; Linda Hammill, Townsend,; Catherine R. Ferenz, Belchertown, all of Mass.

[73] Assignee: BASF Aktiengesellschaft, Federal Republic of Germany, Germany

[21] Appl. No.: 466,265

[22] Filed: Jun. 6, 1995

[51] Int. Cl.$^6$ .......................... C12P 21/02; C07H 21/04; C12N 15/81; C12N 15/85

[52] U.S. Cl. ............... 435/69.1; 435/254.2; 435/255.7; 435/320.1; 435/325; 536/23.1; 536/24.1

[58] Field of Search ................. 435/69.1, 320.1, 435/255.1, 255.7, 240.1, 254.2, 325; 536/23.1, 24.1

[56] References Cited

U.S. PATENT DOCUMENTS

| | | | |
|---|---|---|---|
| 4,992,537 | 2/1991 | Goldberg et al. | 536/23.2 |
| 5,010,003 | 4/1991 | Chang et al. | 435/69.9 |
| 5,162,208 | 11/1992 | Lemoine et al. | 435/69.1 |
| 5,284,768 | 2/1994 | Leqoux et al. | 435/252.33 |
| 5,302,697 | 4/1994 | Goodey et al. | 530/325 |
| 5,389,525 | 2/1995 | Hollenberg et al. | 435/69.1 |

FOREIGN PATENT DOCUMENTS

| | | |
|---|---|---|
| 0 252 854 | 1/1988 | European Pat. Off. . |
| 0 299 108 | 1/1989 | European Pat. Off. . |
| 0 329 127 | 8/1989 | European Pat. Off. . |
| 0 450 430 | 10/1991 | European Pat. Off. . |
| WO 90/13646 | 11/1990 | WIPO . |

OTHER PUBLICATIONS

Baldwin, C., et al., "Structure of cDNA Clones Coding for Human Type ii Procollagen," *Biochem. J.*, vol. 262, 521–528 (1989).

Bernard, M., et al., "Cloning and Sequencing of Pro–α1 (XI) Collagen cDNA Demonstrates that Type XI Belongs to the Fibrillar Class of Collagens and Reveals that the Expression of the Gene is not Restricted to Cartilagenous Tissue," *The Journal of Biological Chemistry*, vol. 263, No. 32, 17159–17166 (1988).

Blumberg, B., et al., "Drosophila Basement Membrane Procollagen α1 (IV)," *The Journal of Biological Chemistry*, vol. 263, No. 34, 18328–18337 (1988).

Brake, A., et al., "α–Factor–directed Synthesis and Secretion of Mature Foreign Proteins in Saccharomyces cerevisiae," *Proc. Natl. Acad. Sci. USA*, vol. 81, 4642–4646 (1984).

Caulagi, V., et al., "Isolation and Partial Sequence of a Collagen Gene from the Human Filarial Parasite Brugia Malayi,"*Molecular and Biochemical Parasitology*, vol. 45, 57–64 (1991).

Elima, K., et al., "The Mouse Collagen X Gene: Complete Nucleotide Sequence, Exon Structure and Expression Pattern,"*Biochem J.*,vol. 289, 247–253 (1993);

Exposito, J., et al., "Cloning and Sequencing of a Porifera Partial cDNA Coding of a Short–chain Collagen," *Eur. J. Biochem.*, vol. 190, 401–406 (1990).

Finer, M., et al., "Construction and Characterization of cDNA Clones Encoding the 5' end of the Chicken Pro α1(I) Collagen mRNA," *Gene*, Vol. 56, 71–78 (1987).

French, B., et al., "Nucleotide Sequence of a cDna Clone for Mouse proα1 (I) Collagen Protein," *Gene*,vol. 39, 311–312 (1995).

Glumoff, V., et al., "Cloning of cDNA for Rat proα1 (III) Collagen mRNA. Different Expression Patterns of Type I and Type III Collagen and Fibronectin Genes in Experimental Granulation Tissue, " *Biochimica et Biophysica Acta*,vol. 1217, 41–48 (1994);.

Janowicz, Z., et al., "Simultaneous Expression of the S and L Surface Antigens of Hepatitis B, and Formation of Mixed Particles in the Methylotrophic Yeast, Hansenula polymorpha," *Yeast*, vol. 7, 431–443 (1991).

Kamagata, Y., et al., "Isolation and Sequencing of cDNAs and Genomic DNAs Encoding the α4 Chain of Basement Membrane Collagen Type IV and Assignment of the Gene to the Distal Long Arm of Human Chromosome 2," *The Journal of Biological Chemistry*,vol. 267, No. 33, 23753–23758 (1992).

Kimura, T., et al., "Molecular Cloning of Rat and Human Type IX Collagen cDNA and Localization of the α1(IX) Gene on the Human Chromosome 6," *Eur. J. Biochem.*,vol. 179, 71–78 (1989).

Kimura, T., et al., "The Human α2(XI) Collagen (COL 11A2) Chain, " *The Journal of Biological Chemistry*,vol. 264, No. 23, 13910–13916 (1989).

Kingston, I., et al., "Comparison of Collagen Gene Sequences in Ascaris suum and Caenorhabditis elegans," *Molecular and Biochemical Parasitology*, vol. 37, 137–146 (1989);

Kuivaniemi, H., et al., "Structure of a Full–length cDNA Clone for the Preproα2(I) Chain of Human Type I Procollagen," *Biochem. J.*,vol. 252, 633–640 (1988).

Li, K., et al., "cDNA Cloning and Chromosomal Mapping of the Mouse Type VII Collagen Gene (Col7a 1): Evidence for Rapid Evolutionary Divergence of the Gene," *Genomics*, vol. 16, 733–739 (1993).

Mayne, R. and Brewton, R., "New Members of the Collagen Superfamily," *Current Opinion in Cell Biology*, vol. 5, 883–890 (1993).

(List continued on next page.)

*Primary Examiner*—Nancy Degen
*Attorney, Agent, or Firm*—Lahive & Cockfield; Giulio A. DeConti, Jr.; Catherine J. Kara, Phd.

[57] ABSTRACT

Hybrid genes comprising a nucleotide sequence encoding a preprocollagen signal sequence operatively linked to a nucleotide sequence encoding a heterologous protein are disclosed. The hybrid genes are useful for secretion of heterologous proteins from host cells. In a preferred embodiment, the signal sequence of the human preprocollagen α1(I) protein is linked to a heterologous protein of interest to allow for secretion of the protein from *Hansenula polymorpha* cells.

39 Claims, 7 Drawing Sheets

OTHER PUBLICATIONS

Metsäranta, M., et al., "Mouse Type II Collagen Gene," *The Journal of Biological Chemistry*, vol. 266, No. 25, 16862–16869 (1991).

Nath, P., et al., "Isolation of an α1 Type–IV Collagen cDNA Clone Using a Synthetic Oligodeoxynucleotide," *Gene*, vol. 43, 301–304 (1986).

Oh, S., et al., "Cloning of cDNA and Genomic DNA Encoding Human Type XVIII Collagen and Localization of α1(XVIII) Collagen Gene to Mouse Chromosome 10 and Human Chromosome 21," *Genomics*, vol. 19, 494–499 (1994).

Palmiter, R., et al., "$NH_2$ –terminal Sequence of the Chick Proα1(I) Chain Synthesized in the Reticulocyte Lysate System," *The Journal of Biological Chemistry*, vol. 254, No. 5, 1433–1436 (1979).

Parente, M., et al., "Human Type VII Collagen: cDNA Cloning and Chromosomal Mapping of the Gene," *Proc. Natl. Acad. Sci. USA*, vol. 88, 6931–935 (1991).

Perälä, M., et al., "Molecular Cloning of the Human α2(IX) Collagen cDNA and Assignment of the Human COL9A2 Gene to Chromosome 1," *FEBS*, vol. 319, No. 1,2, 177–180 (1993).

Phillips, C., et al., "Sequence Analysis of a Full–Length cDNA for the Murine proα2(I) Collagen Chain: Comparison of the Derived Primary Structure with Human proα2(I) Collagen," *Genomics*, vol.13, 1345–1346 (1992).

Roggenkamp, R., et al., "Transformation of the Methylotrophic Yeast Hansenula Polymorpha by Autonomous Replication and Integration Vectors," *Mol. Gen. Genet.*, vol. 202, 302–308 (1986).

Sibley, M., et al., "Genetic Identification, Sequence, and Alternative Splicing of the *Caenorhabditis elegans* α2(IV) Collagen Gene," *The Journal of Cell Biology*, vol. 123, No.1, 255–264 (1993).

Sugimoto, M., et al., "cDNA Isolation and Partial Gene Structure of the Human 4(IV) Collagen Chain, " *FEBS*, vol.330, no. 2, 122–128 (1993).

Toman, P.D. and de Crombrugghe, B., "The Mouse Type–III Procollagen–encoding Gene: Genomic Cloning and Complete DNA Sequence," *Gene*, vol. 147, 161–168 (1994).

Toman, P.D., et al., "Nucleotide Sequence of a cDNA Coding for the Amino –terminal Region of Human Prepro α 1(III) Collagen," *Nucleic Acids Research*, vol. 16, no. 14, 7201 (1988).

Tomita, M., et al., "Characterizations of Sea Urchin Fibrillar Collagen and its cDNA Clone," *Biochimica et Biophysica Acta*, vol. 1217, 131–140 (1994).

Tromp, G., et al., "Structure of a Full–length cDNA Clone for the Preproα1(I) Chain of Human Type I Procollagen," *Biochem. J.*, vol. 253, 919–922 (1988).

Van Der Rest, M. and Garrone, R., "Collagen Family of Proteins," *The FASEB Journal*, vol. 5, 2814–2823 (1991).

Yamada, Y., et al., "A Uniquely Conserved Regulatory Signal is Found Around the Translation Initiation Site in Three Different Collagen Genes," *The Journal of Biological Chemistry*, vol. 258, No. 24, 14914–14919 (1983).

Fellinger et al. (1991), Yeast 7: 463–473.

Romanos et al. (1992), Yeast 8: 423–488.

Kaiser et al. (1987), Science 235: 312–317.

Madison et al. (1992), Gene 121: 179–180.

Chu, M.-L., de Wet, W., Bernard, M., Ding, J.-F., Morabito. M., Myers J., Williams, C., and Ramirez, F. 1984. Human pro α I (I) collagen gene structure reveals evolutionary conservation of a pattern of introns exons. *Nature* 310:337–340. 26, Jul. 1984.

Dickson, L.A., de wet, W.d, 12. berto, M-, Weil, D-, and Ramirez, F. 1985. Analysis at the promoter region and the N–propeptide domain of the human pro α2 (±) collagen gene, Nucleic Acids Research. 13(10): 3427–3438.

1862

TTTGAATTC ATG TTC TCC TTC GTC GAC CTG AGA CTG CTC CTT CTG CTC
GAATTC ATG TTC TCC TTC GTC GAC CTG AGA CTG CTC CTT CTG CTC
CTTAAG TAC AAG AGG CAG CTG GAC TCT GAC GAG GAC GAG
            Met Phe Ser Phe Val Asp Leu Arg Leu Leu Leu Leu Leu

GCC GCC ACC GCG CTG CTG ACC CAC GGC
CGG CGG CGC GAC TGG GAC GTG CCG
Ala Ala Thr Ala Leu Leu Thr His Gly

CGC GAC GAC TGG GTG CCG CAA CAA ATG TGA CTG ACG TG  #2030

```
GCG CTG ACC CAC GGC GTT GTT TAC ACT GAC TGC
                    GTT GTT TAC ACT GAC TGC ACT GAA TCC GGT CAG AAC CTG TGC CTG
                    CAA CAA ATG TGA CTG ACG TGA CTT AGG CCA GTC TTG GAC ACG GAC
                    Val Val Tyr Thr Asp Cys Thr Glu Ser Gly Gln Asn Leu Cys Leu

TGC GAA GGC TCT AAC GTT TGC GGC CAG AAC AAA TGC ATC CTG GGC TCT AAA GGC GAA CGT
ACG CTT CCG AGA TTG CAA ACG CCG GTC TTG TTT ACG TAG GAC CCG AGA TTT CCG CTT GCA
Cys Glu Gly Ser Asn Val Cys Gly Gln Asn Lys Cys Ile Leu Gly Ser Lys Gly Glu Arg

AAC CAG TGC GTT ACT GGC GAA GGT ACC CCG CGT CCG CAG TCT CAC AAC GAC GGC GAC TTC GAA
TTG GTC ACG CAA TGA CCG CTT CCA TGG GGC GCA GGC GTC AGA GTG TTG CTG CCG CTG AAG CTT
Asn Gln Cys Val Thr Gly Glu Gly Thr Pro Arg Pro Gln Ser His Asn Asp Gly Asp Phe Glu

GAA ATC CCG GAA GAA TAC CTG ATG GAC CTT CAG TAA TAGGGATCC
CTT TAG GGC CTT ATG GAC CTT CTT ATG GAC GTC ATT ATCCCTAGG
Glu Ile Pro Glu Glu Tyr Leu Met Asp Leu Gln ***
  G GGC CTT ATG GAC GTC GAC GTC ATT ATCCCTAGGGGG
```

1862
EcoR1
TTTGAATTC ATG TTC TCC TTC GTC
TTTGAATTC ATG TTC TCC TTC GTC GAC CTG AGA CTG CTC CTT CTG GCC GCC ACC
AAAACTTAAG TAC AAG AGG AAG CAG CTG GAC TCT GAC GAG GAA GAC CGG TGG
                Met Phe Val Asp Leu Arg Leu Leu Leu Leu Ala Ala Thr

GCG CTG CTG ACC CAC GGC GTT GTT TAC ACT GAC TGC AC
CGC GAC GAC TGG GTG CCG CAA ATG TGA CTG ACG TG
Ala Leu Leu Thr His Gly Val Val Tyr Thr Asp Cys

GCG CTG CTG ACC CAC GGC GTT GTT TAC ACT GAC TGC ACT GAA TCC GGT CAG AAC CTG
CGC GAC GAC TGG GTG CCG CAA CAA ATG TGA CTG ACG TGA CTT AGG CCA GTC TTG GAC
Ala Leu Leu Thr His Gly Val Val Tyr Thr Asp Cys Thr Glu Ser Gly Gln Asn Leu

TGC CTG TGC GAA GGC TCT AAC GTT TGC GGC CAG GGC AAC AAA TGC ATC CTG GGC TCT
ACG GAC ACG CTT CCG AGA TTG CAA ACG CCG GTC CCG TTG TTT ACG TAG GAC CCG AGA
Cys Leu Cys Glu Gly Ser Asn Val Cys Gly Gln Gly Asn Lys Cys Ile Leu Gly Ser

FIGURE 1C

```
AAA GGC GAA CGT AAC CAG TGC GTT ACT GGC GAA GGT ACC CCG CGT CCG CAG TCT CAC
TTT CCG CTT GCA TTG GTC ACG CAA TGA CCG CTT CCA TGG GGC GCA GGC GTC AGA GTG
Lys Gly Glu Arg Asn Gln Cys Val Thr Gly Glu Gly Thr Pro Arg Pro Gln Ser His

BamHI
AAC GAC GGC GAC TTC GAA GAA ATC CCG GAA GAA TAC CTG CAG TAA TAGGGATCC
TTG CTG CCG CTG AAG CTT TAG GGC CTT CTT ATG GAC GTC ATT ATCCCTAGG
Asn Asp Gly Asp Phe Glu Glu Ile Pro Glu Glu Tyr Leu Gln ***

G GGC CTT CTT ATG GAC GTC ATT ATCCCTAGGGGG
                                              #2302
```

FIGURE 1D

| AmAcid | Codon | Number | /1000 | Fraction |
|---|---|---|---|---|
| Gly | GGG | 32.00 | 7.71 | 0.09 |
| Gly | GGA | 103.00 | 24.83 | 0.30 |
| Gly | GGT | 88.00 | 21.21 | 0.26 |
| Gly | GGC | 120.00 | 28.92 | 0.35 |
| Glu | GAG | 153.00 | 36.88 | 0.64 |
| Glu | GAA | 87.00 | 20.97 | 0.36 |
| Asp | GAT | 77.00 | 18.56 | 0.33 |
| Asp | GAC | 153.00 | 36.88 | 0.67 |
| Val | GTG | 90.00 | 21.69 | 0.28 |
| Val | GTA | 36.00 | 8.68 | 0.11 |
| Val | GTT | 81.00 | 19.52 | 0.25 |
| Val | GTC | 117.00 | 28.20 | 0.36 |
| Ala | GCG | 54.00 | 13.02 | 0.17 |
| Ala | GCA | 59.00 | 14.22 | 0.19 |
| Ala | GCT | 72.00 | 17.35 | 0.23 |
| Ala | GCC | 128.00 | 30.85 | 0.41 |
| Arg | AGG | 33.00 | 7.95 | 0.12 |
| Arg | AGA | 98.00 | 23.62 | 0.35 |
| Ser | AGT | 28.00 | 6.75 | 0.08 |
| Ser | AGC | 42.00 | 10.12 | 0.13 |
| Lys | AAG | 134.00 | 32.30 | 0.74 |
| Lys | AAA | 47.00 | 11.33 | 0.26 |
| Asn | AAT | 31.00 | 7.47 | 0.22 |
| Asn | AAC | 112.00 | 26.99 | 0.78 |
| Met | ATG | 71.00 | 17.11 | 1.00 |
| Ile | ATA | 14.00 | 3.37 | 0.08 |
| Ile | ATT | 61.00 | 14.70 | 0.35 |
| Ile | ATC | 99.00 | 23.86 | 0.57 |
| Thr | ACG | 38.00 | 9.16 | 0.21 |
| Thr | ACA | 32.00 | 7.71 | 0.17 |
| Thr | ACT | 40.00 | 9.64 | 0.22 |
| Thr | ACC | 74.00 | 17.84 | 0.40 |

FIGURE 2A

| AmAcid | Codon | Number | /1000 | Fraction |
|---|---|---|---|---|
| Trp | TGG | 52.00 | 12.53 | 1.00 |
| End | TGA | 14.00 | 3.37 | 0.54 |
| Cys | TGT | 36.00 | 8.68 | 0.35 |
| Cys | TGC | 66.00 | 15.91 | 0.65 |
| End | TAG | 3.00 | 0.72 | 0.12 |
| End | TAA | 9.00 | 2.17 | 0.35 |
| Tyr | TAT | 37.00 | 8.92 | 0.31 |
| Tyr | TAC | 81.00 | 19.52 | 0.69 |
| Leu | TTG | 43.00 | 10.36 | 0.12 |
| Leu | TTA | 11.00 | 2.65 | 0.03 |
| Phe | TTT | 57.00 | 13.74 | 0.40 |
| Phe | TTC | 86.00 | 20.73 | 0.60 |
| Ser | TCG | 83.00 | 20.00 | 0.25 |
| Ser | TCA | 16.00 | 3.86 | 0.05 |
| Ser | TCT | 73.00 | 17.59 | 0.22 |
| Ser | TCC | 90.00 | 21.69 | 0.27 |
| Arg | CGG | 33.00 | 7.95 | 0.12 |
| Arg | CGA | 49.00 | 11.81 | 0.18 |
| Arg | CGT | 33.00 | 7.95 | 0.12 |
| Arg | CGC | 32.00 | 7.71 | 0.12 |
| Gln | CAG | 112.00 | 26.99 | 0.63 |
| Gln | CAA | 65.00 | 15.67 | 0.37 |
| His | CAT | 44.00 | 10.60 | 0.31 |
| His | CAC | 100.00 | 24.10 | 0.69 |
| Leu | CTG | 122.00 | 29.40 | 0.33 |
| Leu | CTA | 23.00 | 5.54 | 0.06 |
| Leu | CTT | 80.00 | 19.28 | 0.22 |
| Leu | CTC | 91.00 | 21.93 | 0.25 |
| Pro | CCG | 26.00 | 6.27 | 0.13 |
| Pro | CCA | 81.00 | 19.52 | 0.40 |
| Pro | CCT | 57.00 | 13.74 | 0.28 |
| Pro | CCC | 40.00 | 9.64 | 0.20 |

FIGURE 2B

COMPOSITIONS FOR EXPRESSION OF PROTEINS IN HOST CELLS USING A PREPROCOLLAGEN SIGNAL SEQUENCE

BACKGROUND OF THE INVENTION

Proteins that are secreted from a cell through a cell membrane are generally produced within the cell in a precursor form, referred to as a "preprotein" that includes an additional peptide sequence at the amino-terminus which is thought to assist the protein in traversing the membrane. This additional peptide sequence is referred to as a "signal sequence" or "leader sequence". Deletion of the signal sequence from a protein prevents its secretion (see e.g., Benson, S. A. et al. (1985) *Ann. Rev. Biochem.* 54:101–134). In eukaryotic cells, preproteins containing a signal sequence are inserted through the membrane of the rough endoplasmic reticulum (RER), thereby directing the preprotein into the secretory pathway. During this process, the signal sequence interacts with a particle called the signal recognition particle (SRP), which in turn is recognized by an RER membrane protein referred to as an SRP receptor or docking protein. After or simultaneous with insertion of the preprotein into the RER, the signal sequence is cleaved from the preprotein by an enzyme called a signal peptidase, thereby releasing the mature protein into the RER. Once proteins are segregated into the lumen of the ER, they migrate to the Golgi apparatus and then to secretory vesicles. Fusion of the secretory vesicles with the plasma membrane releases the contents of vesicle into the extracellular environment. In organisms having both a plasma membrane and a cell wall, e.g., yeast, the vesicle contents typically are released into the periplasmic space between the membrane and the cell wall.

Although signal sequences of secretory proteins share some general features, e.g., typically a short chain amino acid at the carboxyl end and a hydrophobic central region, no uniform consensus sequence exists for the vast array of secreted proteins (see e.g., Watson, M. E. E. (1984) *Nucl. Acids. Res.* 12:5145–5164). In fact, the primary structure of signal sequences of different secreted proteins vary considerably, both among secreted proteins of the same species and secreted proteins of different species. This suggests that each secreted protein has evolved with a particular signal sequence that is well suited for its own translocation across a cell membrane.

The development of recombinant DNA technology has provided a means for expressing recombinant proteins in host cells, often in large quantities. In such expression systems, the ability to efficiently produce a recombinant protein in a secreted form is highly desirable, since the secreted protein can then be recovered from a medium in which the host cells are growing. However, this process often does not function to the degree desired, for example because the native signal sequence of the recombinant protein does not operate well in the host cell. Accordingly, attempts have been made to increase the efficiency of secretion of recombinant proteins by varying which signal sequence is used to direct the secretion of the protein. For example, signal sequences from yeast proteins, such as the signal sequence of the precursor of the yeast mating pheromone a-factor, have been used to direct secretion of non-yeast proteins in yeast host cells (Brake, et al. (1984) *Proc. Natl. Acad. Sci. USA* 81:4642–4646; see also U.S. Pat. No. 5,010,003 by Chang et al.). Although certain signal sequences have been identified which may be useful for the secretion of certain proteins, there is still a need for additional signal sequences that can promote efficient secretion of heterologous proteins.

SUMMARY OF THE INVENTION

This invention provides compositions and methods for expressing heterologous proteins in host cells using a preprocollagen signal sequence. The compositions and methods of the invention allow for secretion of the heterologous protein from the host cell and subsequent recovery of the protein from the extracellular environment.

One aspect of the invention pertains to hybrid genes comprising a first nucleotide sequence encoding a preprocollagen signal sequence operatively linked to a second nucleotide sequence encoding a heterologous protein of interest. A hybrid gene of the invention is inserted into an expression vector, which is then introduced into a host cell to allow for secretion of the protein of interest from the host cell.

In a particularly preferred embodiment, a protein of interest is expressed in the yeast *Hansenula polymorpha* using an expression vector containing a hybrid gene comprising a nucleotide sequence encoding the signal sequence of the human preprocollagen α1(I) protein operatively linked to a nucleotide sequence encoding the heterologous protein of interest. A preferred hybrid gene encodes the preprocollagen signal sequence linked to the protein hirudin.

Expression vector and host cell compositions, and methods of producing proteins in host cells using these compositions, are also encompassed by the invention.

BRIEF DESCRIPTION OF THE DRAWINGS

FIG. 1 illustrates the nucleotide sequences of the primers and templates used to create a hybrid gene composed of a nucleotide sequence encoding a preprocollagen signal sequence operably linked to a nucleotide sequence encoding hirudin, as described in Example 2.

FIG. 2 is a table illustrating codon usage in *H. polymorpha* compiled from the codon usage in five *H. polymorpha* genes.

DETAILED DESCRIPTION OF THE INVENTION

Figure 3:
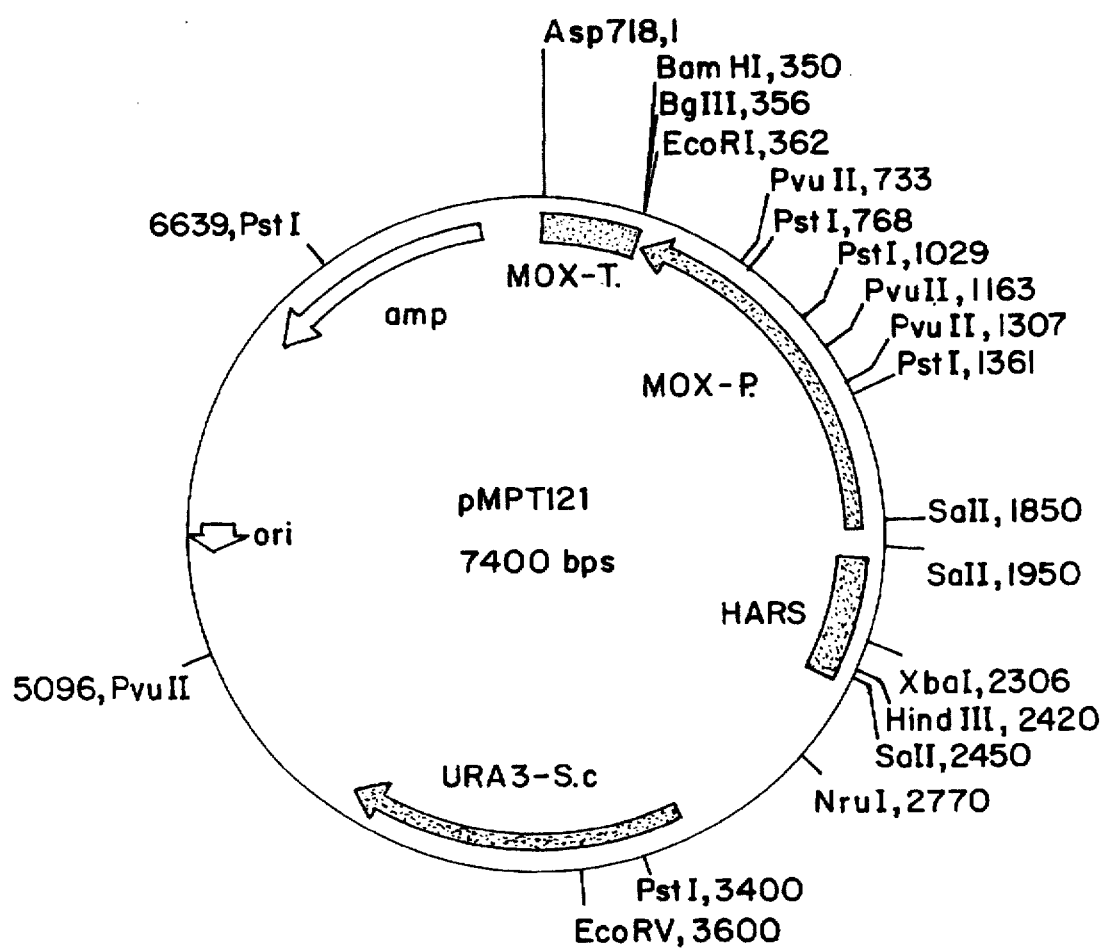
FIG. 3 is a schematic diagram of the *Hansenula polymorpha* expression vector pMPT121.

This invention pertains to compositions and methods for expressing heterologous proteins in host cells using a preprocollagen signal sequence. While applicable to a variety of host cells, the compositions of the invention are particularly useful for expressing heterologous proteins in the methylotrophic yeast *Hansenula polymorpha*. As described in detail herein, it has now been discovered that *H. polymorpha* naturally secrete a collagen-like protein (see Example 1). Moreover, it has further been discovered that the signal sequence of preprocollagen proteins of other species, such as a human preprocollagen signal sequence, functions efficiently in *H. polymorpha* cells to direct the secretion of heterologous proteins from the cells. Various aspects of the invention are described in further detail in the following subsections.

I. Hybrid Genes of the Invention

One aspect of the invention pertains to isolated nucleic acid molecules composed of a first nucleotide sequence encoding a preprocollagen signal sequence operatively linked to a second nucleotide sequence encoding a heterologous protein of interest. Such nucleic acid molecules are also referred to herein as "hybrid genes".

The language "nucleic acid molecule" molecule is intended to encompass DNA and RNA, although a preferred nucleic acid molecule is a double-stranded DNA molecule. An "isolated" nucleic acid molecule is free of sequences which naturally flank the nucleic acid (i.e., sequences located at the 5' and 3' ends of the nucleic acid) in a natural environment (e.g., genomic DNA of an organism from which the nucleic acid is derived). Moreover, an "isolated" nucleic acid molecule may be free of other cellular material.

The hybrid genes of the invention contain a nucleotide sequence encoding a preprocollagen signal sequence. As used herein, the language "signal sequence" refers to an amino-terminal portion of a preprotein that assists in the translocation of a preprotein across a membrane. A "signal sequence" as used herein is synonymous with a "leader sequence". The language "collagen" is intended to include structural macromolecules of the extracellular matrix that include in their structure at least one domain having a characteristic triple helical conformation (for review see e.g., Van der Rest, M. et al. (1991) *FASEB J.* 5:2814–2823; Mayne, R. et al. (1993) *Curr. Opin. Cell Biology* 5:883–890). Collagens are typically characterized by the presence of Gly-Pro-Pro repeats. At least eighteen or nineteen different collagen types have been identified and are intended to be encompassed by the term "collagen". The term "preprocollagen" is intended to include precursor forms of collagen molecules that include a signal sequence and the term "preprocollagen signal sequence" is intended to refer to this signal sequence of the precursor form of collagen.

In a preferred embodiment, the preprocollagen signal sequence is derived from a Type I collagen. A consensus amino acid sequence for a Type I collagen signal sequence, compiled from the amino acid sequences of human α1(I) collagen (as disclosed in Tromp, G. et al. (1988) *Biochem. J.* 253:919–922), chick α1(I) collagen (as disclosed in Yamada, Y. et al. (1983) *J. Biol. Chem.* 258:14914–14919), human α2(I) collagen (as disclosed in Kuivaniemi, H. et al. (1988) *Biochem. J.* 252:633–640), chick α2(I) collagen (as disclosed in Yamada, Y. et al., supra) and mouse α2(I) collagen (as disclosed in Phillips, C. L. et al. (1992) *Genomics* 13:1345–1346), is shown below (standard three-letter abbreviations are used for amino acid residues):

Met-$Xaa_1$-Ser-Phe-Val-Asp-$Xaa_2$-Arg-$Xaa_3$-Leu-Leu-Leu-$Xaa_4$-Ala-$Xaa_5$-Thr-$Xaa_6$-$Xaa_7$-Leu-$Xaa_8$-$Xaa_9$-$Xaa_{10}$. (SEQ ID NO:1), wherein $Xaa_1$ is Phe or Leu, $Xaa_2$ is Leu, Ser or Thr, $Xaa_3$ is Leu, Ile or Thr, $Xaa_4$ is Leu or Ile, $Xaa_5$ is Ala or Val, $Xaa_6$ is Ala, Val, Ser or Leu, $Xaa_7$ is Leu, Tyr or Cys, $Xaa_8$ is Thr or Ala, $Xaa_9$ is His, Arg or Thr and $Xaa_{10}$ is Gly, Cys or Ser.

In a preferred embodiment, the preprocollagen signal sequence encoded by the hybrid gene is derived from a human α1(I) collagen (as disclosed in Tromp, G. et al., supra) and preferably has the following amino acid sequence:

Met-Phe-Ser-Phe-Val-Asp-Leu-Arg-Leu-Leu-Leu-Leu-Leu-Ala-Ala-Thr-Ala-Leu-Leu-Thr-His-Gly. (SEQ ID NO: 2)

Alternatively, the preprocollagen signal sequence can be derived from other types of collagen, for example a Type II, Type III or Type X collagen. A consensus amino acid sequence for a Type II collagen signal sequence, compiled from the amino acid sequences of human α1(II) collagen (as disclosed in Baldwin, C. T. et al. (1989) *Biochem. J.* 262:521–528) and mouse α1(II) collagen (as disclosed in Metsäranta, M. et al. (1991) *J. Biol. Chem.* 266:16862–16869), is shown below:

Met-Ile-Arg-Leu-Gly-Ala-Pro-Gln-Ser-Leu-Val-Leu-Leu-Thr-Leu-Leu-$Xaa_1$-Ala-Ala-Val-Leu-Arg-Cys (SEQ ID NO: 3), wherein $Xaa_1$ is Val or Ile.

A consensus amino acid sequence for a Type III collagen signal sequence, compiled from the amino acid sequences of human eel (III) collagen (as disclosed in Toman, P. D. et al. (1988) *Nucl. Acids. Res.* 16:7201), chick α1(III) collagen (as disclosed in Yamada, Y. et al., supra) and mouse α1(III) collagen (as disclosed in Toman, P. D. et al. (1994) *Gene* 147: 161–168), is shown below:

Met-Met-Ser-Phe-Val-Gln-$Xaa_1$-$Xaa_2$-$Xaa_3$-$Xaa_4$-$Xaa_5$-$Xaa_6$-Leu-$Xaa_7$-$Xaa_8$-$Xaa_9$-$Xaa_{10}$-Pro-$Xaa_{11}$-$Xaa_{12}$-Ile-Leu-Ala-Gln (SEQ ID NO: 4), wherein $Xaa_1$ is Lys or Ser, $Xaa_2$ is Gly or Val, $Xaa_3$ is Ser or Thr, $Xaa_4$ is Trp or Leu, $Xaa_5$ is Leu or Phe, $Xaa_6$ is Leu or Ile, $Xaa_7$ is Ala or Thr, $Xaa_8$ is Leu or Val, $Xaa_9$ is Leu or Phe, $Xaa_{10}$ is His or Gln, $Xaa_{11}$ is Thr or Ser and $Xaa_{12}$ is Ile, Val or Leu.

A consensus amino acid sequence for a Type X collagen signal sequence, compiled from the amino acid sequences of human α1(X) collagen (as disclosed in Elima, K. et al. (1993) *Biochem. J.* 289:247–253), chick α1(X) collagen (as disclosed in Elima, K et al., supra), bovine α1(X) collagen (as disclosed in Elima, K. et al., supra) and mouse α1(X) collagen (as disclosed in Elima, K. et al., supra), is shown below:

Met-Leu-Pro-Gln-$Xaa_1$-$Xaa_2$-$Xaa_3$-Leu-Leu-Leu-$Xaa_4$-$Xaa_5$-Asp-$Xaa_6$-$Xaa_7$-Val-His-Gly (SEQ ID NO: 5), wherein $Xaa_1$ is Ile or Thr, $Xaa_2$ is Pro, Ala or Ser, $Xaa_3$ is Pro or Leu, $Xaa_4$ is Met or Phe, $Xaa_5$ is Phe, Ser or Cys, $Xaa_6$ is Thr or Asn and $Xaa_7$ is Leu or Ile.

The preprocollagen signal sequence encoded by the hybrid gene can be derived from a mammalian collagen (e.g., human, mouse, bovine, as described above) or an avian collagen (e.g., chick, as described above). Moreover, signal sequences derived from collagens of other species are also encompassed by the invention. For example, collagens have been described in *Drosophila melanogaster* (see e.g., Blumberg, B. et al. (1988) *J. Biol. Chem.* 34:18328–18337), the nematode *Caenorhabditis elegans* (see e.g., Sibley, M. H. et al. (1993) *J. Cell Biol.* 123:255–264), the nematode *Ascaris suum* (see e.g., Kingston, I. B. et al. (1989) *Mol. Biochem. Parasitol.* 37:137–146), the sea urchin species *Hemicentrotus pulcherrimus*, *Strongylocentrotus purpuratus* and *Asthenosoma ijimai* (see e.g., Tomita, M. et al. (1994) *Biochim. Biophys. Acta* 1217:131–140), the filarial parasite *Brugia malayi* (see e.g, Caulagi, V. R. et al. (1991) *Mol. Biochem. Parasitol.* 45:57–64) and Porifera sponges (see e.g., Exposito, J. et al. (1990) *Eur. J. Biochem.* 190:401–406). Examples of preprocollagen signal sequences from lower eukaryotes include the signal sequence of the *D. melanogaster* α1(IV) collagen (as disclosed in Blumberg, B. et al., supra), having the following amino acid sequence:

Met-Leu-Pro-Phe-Trp-Lys-Arg-Leu-Leu-Tyr-Ala-Ala-Val-Ile-Ala-Gly-Ala-Leu-Val-Gly-Ala-Asp-Ala (SEQ ID NO: 6)

and the *C. elegans* α2(IV)-derived signal sequence (as disclosed in Sibley, M. H. et al, supra) having the following amino acid sequence:

Met-Lys-Gln-Arg-Ala-Ala-Leu-Gly-Pro-Val-Leu-Arg-Leu-Ala-Ile-Leu-Ala-Leu-Leu-Ala-Val-Ser-Tyr-Val-Gln-Ser (SEQ ID NO: 7).

Furthermore, as described further in Example 1, a secreted collagen-like molecule has been detected in culture medium of the yeast *H. polymorpha*, indicating that yeast species likely carry collagen or collagen-like genes. Accordingly, preprocollagen signal sequences derived from yeast collagen or collagen-like proteins are also encompassed by the invention.

In addition to a first nucleotide sequence encoding a preprocollagen signal sequence, the hybrid genes of the invention also contain a second nucleotide sequence encoding a heterologous protein of interest. The second nucleotide sequence is operably linked to the first nucleotide sequence. As used herein, the term "operably linked" is intended to mean that the two nucleotide sequences are connected in manner such that, upon transcription of the hybrid gene and translation of the resultant mRNA, a hybrid protein comprised of the preprocollagen signal sequence linked to the heterologous protein of interest is produced. For example, a DNA molecule comprising the first nucleotide sequence is ligated, in a 5' to 3' orientation, to another DNA molecule comprising the second nucleotide sequence such that, after ligation, the translational frames of the encoded signal sequence and protein are not altered (i.e., the DNA molecules are ligated to each other "in-frame"), thereby creating a hybrid gene encoding a fusion protein composed of the signal sequence and the protein of interest. Alternative to ligation of two separate DNA molecules, a hybrid gene of the invention can be produced by standard polymerase chain reaction techniques, for example as described in detail in Example 2 and illustrated in FIG. 1.

The second nucleotide sequence of the hybrid gene of the invention encodes a heterologous protein of interest. The term "heterologous", as used in reference to the protein of interest encoded by the hybrid gene, is intended to mean that the protein of interest differs from the protein from which the preprocollagen signal sequence is derived, i.e., the protein of interest is not a collagen. However, in relationship to the host cell in which the protein is expressed, the protein may be either heterologous to the host cell (i.e., a protein may be from a different species than the host cell) or homologous to the host cell (i.e., a protein may be from the same species as the host cell). The hybrid genes of the invention can encode a wide variety of proteins of interest. The protein of interest may be a protein that naturally is secreted by cells (i.e., a soluble protein that naturally is produced as a preprotein having a native signal sequence). In this case, the native signal sequence of the protein is replaced by a preprocollagen signal sequence in the hybrid gene. Alternatively, the protein of interest may be a protein that naturally is a cytoplasmic protein (i.e., the protein does not naturally contain a signal sequence). In this case, the preprocollagen signal sequence is linked to the amino terminus of the protein to thereby transform the protein into a secreted form. A preferred protein of interest to be expressed using a preprocollagen signal sequence as described herein is the thrombin inhibitory protein hirudin (see Examples 2 and 3). Non-limiting examples of other proteins that may be produced in host cells using the expression system described herein include Factor VIII, Factor IX, insulin, erythropoietin, anti-angiogenesis factors, growth hormone, soluble TNF receptor, interleukins (e.g., IL-2), interferons (e.g., α- or γ-IFN) and other cytokines, growth factors, and antibodies or antibody fragments.

II. Recombinant Expression Vectors

To express a protein of interest in a host cell, a hybrid gene of the invention is typically incorporated into a recombinant expression vector using standard recombinant DNA techniques. Accordingly, another aspect of the invention pertains to recombinant expression vectors carrying a hybrid gene of the invention. As used herein, the term "vector" refers to a nucleic acid molecule capable of transporting another nucleic acid to which it has been linked. Vectors capable of directing the expression of genes to which they are operatively linked are referred to herein as "expression vectors". In general, expression vectors of utility in recombinant DNA techniques are often in the form of a "plasmid" which typically refers to a circular double stranded DNA molecule. In the present specification, "plasmid" and "vector" are used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention (i.e., hybrid gene) in a form suitable for expression of the nucleic acid in a host cell, which means that the recombinant expression vectors includes one or more regulatory sequences, selected on the basis of the host cells to be used for expression, which is operatively linked to the nucleic acid in a manner which allows for expression of the hybrid gene (e.g., in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a gene in many types of host cell, those which direct expression of the gene only in certain types of host cells or organisms (e.g., tissue-specific or species specific regulatory sequences) and those which direct expression of the nucleotide sequence only under certain conditions, referred to herein as "inducible" regulatory sequences. In a preferred embodiment, expression of a hybrid gene of the invention is regulated by an inducible regulatory sequence, thus allowing for control of the timing and/or level of expression of the encoded protein of interest in a host cell. It will be appreciated by those skilled in the art that the design of the expression vector may depend on such factors as the choice of the host cell to be transformed and the level of expression of protein desired.

The recombinant expression vectors of the invention can be designed for expression of a protein of interest in eukaryotic or prokaryotic cells, although preferably the vector is a eukaryotic expression vector. In a particularly preferred embodiment, the expression vector is suitable for expression of the hybrid gene in the methylotrophic yeast *Hansenula polymorpha*. Expression vectors for use in *H. polymorpha* are known in the art, for example, pMPT121, pFPMT121 or pRB (Rhein Biotech, Düsseldorf, Germany)(see e.g., Gellissen, G. et al. ( 1991 ) *Bio/Technology* 9:291–295; Janowicz, et al. ( 1991 ) Yeast 7:431–443; European Patent 173 378 B 1; European Patent 299 108 B 1; European Patent Application 450 430 A2; U.S. Pat. No. 5,389,525). In these vectors, expression of a hybrid gene introduced into the vector is under the control of the MOX alcohol oxidase promoter (pMPT121 ) or the formate dehydrogenase promoter (pFPMT 121 and pRB). The structure of pMPT 121 is illustrated schematically in FIG. 3. Introduction of a hybrid gene into the *H. polymorpha* expression vector pMPT121 is described in further detail in Example 2. To maximize expression of the protein of interest in *H. polymorpha*, the nucleotide sequence encoding the preprocollagen signal sequence and/or the protein of interest can be altered such that the individual codons encoding amino acids are those preferentially utilized in *H. polymorpha*. A codon usage table for *H. polymorpha* has been prepared from five known endogenous *H. polymorpha* genes. This table is shown in FIG. 2. Alteration of nucleotide sequence of a hybrid gene to include codons preferentially utilized in *H. polymorpha* can be carried out by standard DNA mutagenesis techniques.

In addition to *H. polymorpha* expression vectors, other yeast expression vectors (e.g., for expression in *Saccharomyces cerevisiae*) are encompassed by the invention. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Furthermore, mammalian expression vectors are encompassed by the invention. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. Alternatively, the regulatory sequences of the mammalian expression vector may direct expression of the hybrid gene preferentially in a particular cell type (e.g., tissue-specific regulatory elements). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264, 166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546). Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) Nature 296:39–42; Searle et al. (1985) *Mol. Cell Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad Sci. USA* 89:5547–5551; and PCT Publication No. WO 94/29442).

In another embodiment, the recombinant expression vector can be a prokaryotic expression vector, such as a vector suitable for expression of proteins in *Eschericia coli*. Examples of suitable inducible *E. coli* expression vectors include pTrc (Amann et al., (1988) *Gene* 69:301–315) and pET 11 d (Studier et al., *Gene Expression Technology. Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11 d vector relies on transcription from a T7 gn20-lac fusion promoter mediated by a coexpressed viral RNA polymerase (T7 gn1). This viral polymerase is supplied by host strains BL21(DE3) or HMS174(DE3) from a resident γ prophage harboring a T7 gn1 gene under the transcriptional control of the lacUV 5 promoter. To maximize protein expression in *E. coli*, the nucleotide sequence encoding the preprocollagen signal sequence and/or the protein of interest can be altered to reflect preferred codon usage in *E. coli* (see e.g., Wada et al., (1992) *Nuc. Acids Res.* 20:2111–2118). Such alteration of nucleotide sequences can be carried out by standard DNA mutagenesis techniques.

In yet another embodiment, the recombinant expression vector allows for expression of a protein of interest in insect cells (e.g., baculovirus expression vectors). Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

III. Host Cells

Proteins of interest encoded by a hybrid gene of the invention can be expressed by introducing the hybrid gene (e.g., carried in a recombinant expression vector) into a host cell. As used herein, the term "host cell" is intended to include any eukaryotic or prokaryotic cell or cell line so long as the cell or cell line is not incompatible with the protein to be expressed, the selection system chosen or the fermentation system employed. The invention is particularly applicable to expression of proteins in host cells in culture ("in vitro"), although recombinant expression vectors can also be introduced into cells in an organism ("in vivo") to allow for expression of the protein within the organism. Preferred host cells of the invention are yeast and mammalian cells, although other host cells (e.g., bacterial cells, insect cells, etc.) may also be useful for producing proteins of interest in accordance with the invention. A particularly preferred host cell is the methylotrophic yeast *H. polymorpha*, into which a methanol-responsive expression vector such as pMPT121 has been introduced. When *H. polymorpha* cells, carrying pMPT 121 into which a gene of interest has been introduced, are grown in glucose-containing medium, gene expression is repressed. Gene expression can be derepressed by growth in glycerol-containing medium, or alternatively, gene expression can be actively induced by growth of the cells in methanol-containing medium. Mammalian host cells are also encompassed by the invention. Non-limiting examples of mammalian cell lines which can be used include COS cells, CHO dhfr⁻ cells (Urlaub and Chasin (1980) *Proc. Natl. Acad Sci. USA* 77:4216–4220), 293 cells (Graham et al. (1977) *J. Gen. Virol.* 36: pp59) or myeloma cells like SP2 or NS0 (Galfre and Milstein (1981) *Meth. Enzymol.* 73(B) :3–46).

A recombinant expression vector can be introduced into target host cells via conventional techniques known in the art for transducing, transforming or transfecting host cells. As used herein, the terms "transduction", "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, and infection of the host cell with a vital vector. Suitable methods for transducing, transforming or transfecting host cells can be found in Sambrook et al. (*Molecular Cloning: A Laboratory Manual*, 2rid Edition, Cold Spring Harbor Laboratory press (1989)), and other laboratory textbooks. Moreover, a recombinant expression vector can also be transferred into cells in vivo, for example by application of a delivery mechanism suitable for introduction of nucleic acid into cells in vivo, such as retroviral vectors (see e.g., Ferry, Net al. (1991) *Proc. Natl. Acad Sci. USA* 88: 8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc. Natl. Acad. Sci. USA* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166,320), direct injection of DNA (see e.g., Acsadi et al. (1991) *Nature* 332: 815–818; and Wolff et al. (1990) *Science* 247:1465–1468.) or particle bombardment (see e.g., Cheng, L. et al. (1993) *Proc. Natl. Acad Sci. USA* 90:4455–4459; and Zelenin, A. V. et al. (1993) *FEBS Letters* 315:29–32).

The number of host cells transformed with a hybrid gene of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Preferably, the recombinant expression vector includes a selectable marker gene that allows for selection of host cells into which the vector has been introduced. In a preferred embodiment, an auxotrophic host cell is used and the recombinant expression vector carries a gene that complements the deficiency. For example, the *Hansenula polymorpha* strain RB11, (Rhein Biotech, Düsseldorf, Germany),which is a URA3 auxotroph, can be used in conjunction with a vector, e.g., pMPT121, which carries the URA3 gene of *S. cerevesiae*. (see e.g., Roggenkamp, R. et al. (1984) *Mol. Gen. Genet.* 194:489–493; Roggenkamp, R. et al. (1986) *Mol. Gen. Genet.* 202:302–208). As described in Example 3 (parts B through D), the pMPT121 plasmid can be stably integrated into the yeast genome, thereby allowing for stable gene expression in these host cells. Alternative to use of an auxotrophic host cell, a selectable marker such as a gene that confers a drug resistance on the host cell can be used to identify stable transformants. Examples of such selectable markers include those which confer resistance to G418 and hygromycin.

IV. Methods for Producing Proteins

The host cells of the invention are useful for production of a protein of interest. Accordingly, another aspect of the invention pertains to methods of producing proteins using the host cells of the invention. In one embodiment, the method comprises culturing a host cell containing a recombinant expression vector carrying a hybrid gene of the invention such that the heterologous protein of interest is produced by the host cell. Due to the presence of the preprocollagen signal sequence linked to the protein of interest, the protein is secreted by the host cell (e.g., into a culture medium in which the host cell is growing). Thus, in a preferred embodiment, the method of the invention further comprises recovering the protein of interest from a culture medium in which the host cell is growing. When the recombinant expression vector includes an inducible regulatory sequence for control of expression of the hybrid gene, the host cell can be maintained under non-inducing conditions until protein production is desired and then switched to inducing conditions (e.g., an inducing agent can be added to the culture medium) to stimulate expression of the protein in the host cells. The particular conditions for host cell culture and protein expression will vary according to the particular host cell and expression system used, the amount of protein expression desired, etc. Following expression of the protein of interest in the host cell and secretion of the protein from the host cell, the protein can be recovered from the extracellular environment by standard protein purification techniques.

In another embodiment, the invention provides methods for large scale production of proteins. Large scale production of a protein of interest can be accomplished using cultured cells, e.g., yeast cells (preferably *H. polymorpha* cells) in vitro by standard fermentation techniques to produce the protein of interest or, alternatively, large scale production is also possible within a host organism, such as a transgenic animal. Advances in transgenic technology have made it possible to produce transgenic livestock, such as cattle, goats, pigs and sheep (reviewed in Wall, R. J. et al. (1992) *J. Cell. Biochem.* 49:113–120; and Clark, A. J. et al. (1987) *Trends in Biotechnology* 5:20–24). Accordingly, transgenic livestock can be constructed which carrying in their genome a hybrid gene of the invention. Protein production can be targeted to a particular tissue by linking the hybrid gene to an appropriate tissue-specific regulatory element(s) which limits expression of the gene to certain cells. For example, a mammary gland-specific regulatory element, such as the milk whey promoter (U.S. Pat. No. 4,873,316 and European Application Publication No. 264, 166), can be linked to the hybrid gene to limit expression of the protein of interest to mammary tissue such that the protein is secreted into the milk of the transgenic animal, and if desired, the protein can then be isolated from the milk.

This invention is further illustrated by the following examples which should not be construed as limiting. The contents of all references, patents and published patent applications cited throughout this application are hereby incorporated by reference.

EXAMPLE 1

Analysis of Proteins Naturally Secreted by *Hansenula Polymorpha*

In order to discover a new signal sequence which could be used for the expression and secretion of heterologous proteins from the yeast *Hansenula polymorpha*, the naturally secreted proteins found in the liquid media from an induced culture were examined. Five hundred milliliters of semi-rich medium [0.14% Yeast Nitrogen Base without ammonium sulfate, 0.5% ammoniumsulfate, 0.06% potassium dihydrogenphosphate, 0.3% Peptone 5 (Casamino acids), 0.1% Yeast Extract, 0.2% Gelatone] containing 1% glycerol and 400 µl of 0.4% uracil was inoculated with 200 µl of a fresh overnight culture of *H. polymorpha* strain RB 11 is an auxotrophic mutant of *H. polymorpha* (ura3) deficient in orotidine-5-phosphate decarboxylase, homothallic mutant showing stable haploid phase; produced by Rhein Biotech GmbH by ethylmethanesulfonate-mutagenesis as described (Roggenkamp, R. et al. (1986) *Mol. Gen Genet.* 202:302–308) Growth continued for 3 nights at 37 °C., at which point optical density at 600nm=11 ($OD_{600}$). Methanol was added to 1% to simulate inducing conditions (Gellissen, G. et al. (1992) *Biotech. Adv.* 10:179–189), and growth allowed to continue overnight at 37° C. to an $OD_{600}$=16.

The cells were separated from the culture medium by centrifugation of the 500 ml culture for 15 minutes at 5,000 rpm in a Sorvall RC5-B centrifuge at 4° C. The supernatant was decanted, and passed through a 0.45 µm filter to remove any residual cells. The medium was concentrated to 7.5 ml in an Amicon 350 ml filter unit using a YM30 filter under nitrogen at 60 p.s.i. In later cultures, the protease inhibitor phenylmethysulfonylfloride (PMSF) was added to the filtered supernatant for a final concentration of 1 mM.

Seventy microliters of the concentrated sample was mixed with equal volume of 2× Laemmli sample buffer (120 mM Tris pH 6.8, 4.0% sodium dodecyl sulfate (SDS), 20% glycerol, 0.01% bromophenol blue, 1.4 μM β-mercaptoethanol). The sample was boiled 5 minutes, microfuged briefly and loaded onto 8 lanes of a 12% SDS-PAGE 1.5 mm thick gel. Unstained low molecular weight standards from BioRad were run on one outermost lane and a prestained standard on the other. The gel was run overnight at about 50 V until the dyefront reached the bottom of the gel. Two lanes of the gel, including one test sample and the unstained size standard, were cut off from the rest of the gel for coomassie blue staining, which revealed 2 heavy and 2 faintly stained bands at 90, 60, 55, and 35 kDa respectively. The unstained proteins remaining on the gel was transferred onto a ProBlot membrane (P/N 400994, Applied Biosystems-Perkin Elmer) using a wet transfer method. The transfer ran overnight at 100 milliamps at 4° C. with constant stirring of the transfer buffer (25 mM Tris pH 8.3, 1.4% glycine, 10% methanol, 0.01% SDS). Protein bands blotted onto this membrane were identified by Ponceau-S staining (0.1% in 1% acetic acid).

N-terminal sequence of the bands in the 35 KDa and 60 KDa ranges gave multiple sequences which were very low in signal strength but appeared rich in proline and glycine residues. N-terminal sequence of the low molecular weight 35 KDa region from two different blots gave the following sequences:

Pro-Pro*-Gly-Pro-Pro*-Gly-Pro-Pro*-Gly-Pro-Pro*-Gly-Pro-Pro* (SEQ ID NO: 8).

(* indicates a modified PTH- residue on the protein sequencer, which appeared to be proline-related with adducts)

The sequence below (SEQ ID NO: 9) was also obtained from supernatants of cells having higher density to which PMSF was added. An increase in the transfer yield gave stronger sequencing signals of the major proteins, confirming enriched Gly-Pro-Pro.

Gly-Pro-Pro*-Gly-Pro-Pro*-Gly-Pro-Pro*-Gly-Pro-Pro*-Gly (SEQ ID NO: 9)

Protein data base searches were performed using the sequences with the strongest signal strength, assuming the modified residues to be prolines. All matches were homologous to collagen-related proteins in which the third position of each trimer repeat region was a hydroxylated proline. Several similarly produced membranes were subjected to amino acid sequencing where the major 60 kDa and 35 kDa band were repeatedly identified as a collagen-like protein. Thus, these experiments demonstrate the surprising and unexpected result that endogenous collagen-like proteins are produced in H. polymorpha.

EXAMPLE 2

Construction of an H. polymorpha Expression Vector Containing a Preprocollagen Signal Sequence In view of the results described in Example 1 which demonstrated that H. polymorpha naturally secretes a collagen-like protein, a recombinant expression vector for secretion of a protein from H. polymorpha was prepared in which a nucleotide sequence encoding a preprocollagen signal sequence was linked to the gene encoding the heterologous protein.

The signal sequence for the human preprocollagen αb 1(1) protein was used to secrete a heterologous protein, hirudin, from H. polymorpha. The amino acid sequence corresponding to the secretion signal for human preprocollagen α1(1) is as follows: Met-Phe-Ser-Phe-Val-Asp-Leu-Arg-Leu-Leu-Leu-Leu-Leu-Ala-Ala-Thr-Ala-Leu-Leu-Thr-His-Gly (SEQ ID NO: 2).

A. PCR Amplification

Cloning of the human preprocollagen signal sequence-hirudin construct was performed by a three step process utilizing the polymerase chain reaction (PCR), as illustrated in FIG. 1. In the first step, two different fragments were created that together represent the entire human preprocollagen-hirudin gene with overlapping sequences in the middle where the two can be linked, and restriction sites on each end for cloning into the expression vector.

For the first fragment (labelled A in FIG. 1), the template that was used for the amplification reaction was a construct that contained the preprocollagen signal sequence open reading frame attached to another gene. This open reading frame had its codons modified to reflect the preferred codon usage of known H. polymorpha genes, in accordance with the codon usage table set forth in FIG. 2. The 5' primer, #1862, had the following nucleotide sequence: 5-TTT TGA ATT CAT GTT CTC CTT CGT C-3 (SEQ ID NO: 10). This 5' primer is complementary to the human preprocollagen α1( 1 ) signal sequence and contains an EcoRI restriction site. The Y primer, #2030, had the following nucleotide sequence: 5-GTG CAG TCA GTG TAA ACA ACG CCG TGG GTC AGC AGC GC-3 (SEQ ID NO: 11). This 3' primer contains nucleotide sequences corresponding to the amino terminus of the hirudin gene and the carboxy-terminus of the collagen gene. PCR amplification using these two primers and the preprocollagen signal sequence-containing plasmid as a template resulted in a fragment (fragment A of FIG. 1 ) containing the full length preprocollagen signal region linked to the 5' region of the hirudin gene.

For the second fragment, the template that was used for the amplification reaction was a construct that contained the hirudin gene linked to a different signal sequence. The PCR reaction utilized a 5' primer, #2031, having the following nucleotide sequence: 5-GCG CTG CTG ACC CAC GGC GTT GTT TAC ACT GAC TGC-3 (SEQ ID NO: 12). This 5' primer is complementary to the 3' prime region of the collagen signal sequence and the 5' region of the Hirudin gene. The PCR reaction utilized a Y primer, #2032, having the following nucleotide sequence: 5-GGG GGA TCC CTA TTA CTG CAG GTA TTC TTC CGG G-3 (SEQ ID NO: 13). This 3' primer is complementary to the carboxy terminus of the Hirudin gene and includes a BamHI site at the 5' end. PCR amplification using these primers and the hirudin gene-containing plasmid as a template resulted in a fragment (fragment B of FIG. 1) containing the full length hirudin gene preceded by the carboxy terminus of the preprocollagen signal sequence, and followed by the BamHI restriction site for cloning into a vector.

Standard PCR conditions were used to obtain the above mentioned fragments using 30 cycles of 94° C. denaturing step for 30 seconds, annealing for 30 seconds at 52° C., and 60 second elongation at 72° C. These 30 cycles were followed by 5 minutes at 72° C. for final extension. The reactions were then held at 4° C. until ready for further use.

5 μl of each of the appropriate primers at 20 μM concentrations were used in each reaction with the following additional reaction components: 10 μl of standard 10× PCR buffer (containing MgCl₂), from Perkin Elmer, 8 μl of dNTP mix containing 2.5 mM each deoxynucleoside triphosphate (Perkin Elmer), 0.5 μl Taq polymerase (Perkin Elmer) and 61.5 μl dH₂O for a final volume of 100 μl.

The two PCR fragments, fragments A and B, from the two PCR reactions described above, were then separately run out on 2% agarose gels containing 0.5 μg/ml ethidium bromide to visualize the resultant bands under U.V. Light. The expected size bands were observed and purified by electrophoresis into DEAE paper for 10 minutes at 100 V and elution with buffer containing 20% ethanol, 1M LiCl, 10 mM Tris pH 7.5, and 1 mM EDTA. The eluate was then precipitated with isopropanol, pelleted, washed with 70% ethanol, dried by speed vacuum and resuspended in 10 μl dH₂O.

The second step linked Fragment A and Fragment B together. Both fragments from above in 10 μl volumes were combined with 10 μl of PCR buffer, 8 μl nNTP mix, 1 μl Taq polymerase, and 61 μl dH₂O. 15 cycles of the above mentioned PCR procedure were performed and then frozen at −20 C. This created fully-linked molecules (i.e., preprocollagen signal sequence to hirudin sequence) by Taq polymerase-mediated extension of the overlap regions (i.e., complementary regions) of the primers used to amplify fragments A and B.

In the third and final step, the product produced in the linking of Fragments A and B as described above was amplified by cycling 1 μl of the above reaction in the standard 100 μl PCR mix (described above) containing 5 μl oligo #1862 (SEQ ID NO: 10) at 20 μM and 5 μl oligo #2032 (SEQ ID NO: 13) at 20 μM. The cycling method for amplification was the same as used for creating Fragments A and B, described above. The entire PCR reaction was run on a 1% agarose gel containing 0.5 μg/ml ethidium bromide. An approximately 270 b.p. product was visualized and then purified using DEAE paper, as described above.

After purification of the resultant PCR product, the fragment was restriction digested for cloning at 37° C. for 2 hours in a reaction containing the following: 10 μl purified PCR product, 6 μl 10× EcoR1 Buffer (New England Biolabs (NEB), Wellesley, Mass.), 3 μl EcoRI enzyme (60 units) (NEB), 3 μl BamH1 enzyme (60 units) (NEB) and 38 μl dH₂O. The digested fragment was purified from a 1.5% agarose gel containing 0.5 μg/ml ethidium bromide by the DEAE method, as described above.

B. Ligation of Insert into Expression Vector

The preprocollagen signal sequence-hirudin gene was inserted into the *H. polymorpha* expression plasmid pMPT 121 (Rhein Biotech, Düsseldorf, Germany). pMPT 121 consists of the MOX promoter (Ledeboer, A. M. et al. (1985) *Nucl. Acids. Res.* 13:3063–3082; Gellissen, G. et al. (1992) *Biotech. Adv.* 10:179–189) of the methanol oxidase gene and the MOX terminator surrounding a three enzyme restriction digest insertion site for heterologous genes. The URA3 gene from *Saccharomyces cerevisiae* (Roggenkamp, R. et al. (1984) *Mol. Gen. Genet.* 194:489–493; Roggenkamp, R. et al. (1986) *Mol. Gen. Genet.* 202:302–208), and an ampicillin resistance marker are present for selection of yeast and *E. coli* transformants respectively. Both an *E. coli* origin of replication and HARS (*Hansenula polymorpha* autonomous replication sequence), (Roggenkamp et al. (1984) supra, Roggenkamp et al. (1986) supra), are utilized for plasmid replication in their respective hosts. The pMPT121 vector is illustrated schematically in FIG. 3.

pMPT121 (30 μg) was digested first with EcoRI and then with BamHI by standard methods. The plasmid was checked for digest completion on 1% agarose gel, and purified from the gel using 70 μl glassmilk from Gene Clean (BIO 101, Inc.); resulting in approximately 80 μl of digested plasmid at a concentration estimated to be about 300 ng/μl.

A ligation reaction was prepared containing the following reaction components: 5 μl purified preprocollagen signal sequence-hirudin gene insert (prepared as described above), 2 μl 10× Ligase buffer (NEB), 1 μl T4 Ligase (400 units) (NEB) and 11 μl dH₂O. Ligation was carried out overnight at 15 C.

Following the ligation reaction, the products were transformed into competent *E. coli* strain MM294A (K12, F−; endA1 hsdR17 ($r_k$-$m_k^+$)supE44 thi-1 pro-820). Competent MM294A cells were prepared as follows: A three milliliter culture in 2× YT medium (Sambrook, J. et al. (1989) *Molecular Cloning. A Laboratory Manual*, Cold Spring Harbor, New York:Cold Spring Harbor Press) was grown overnight at 37° C., starting from a frozen seed culture. The overnight culture was used to inoculate 250 ml of 2× YT, and grown with shaking at 37° C. until $OD_{600}$=0.5. Cells were harvested by centrifugation for 8 minutes at 3,000 rpm at 0° C. The cell pellet was resuspended in 125 ml ice cold 10 mM MgCl₂, 30 mM CaCl₂, 10% glycerol. One milliliter aliquots were frozen at −80 C until use.

In a pre-chilled tube, 10 μl of the ligation mix of Col-Hirudin expression vector was added to 100 μl of competent MM294A and incubated on ice for 30 minutes. The mixture was heat shocked at 42° C. for 2 minutes, then added to 1 ml of 2× YT medium and incubated for 1 hour at 37° C. Aliquots of 50 μl, 100 μl, and the remaining 850 μl were plated onto Luria-Bertani (LB) plates (Ampicillin, 100 μg/ml) (Sambrook, et al., supra) and incubated overnight at 37° C.

C. Identification of Positive Clones

One hundred twenty-three total colonies were obtained from the transformation. Twenty individual colonies were picked, and patched on to LB ampicillin plates and allowed to grow at room temperature for 3 nights. Screening was originally done by PCR in 25 μl PCR reactions using 0.5 μl each of primers #1862 (SEQ ID NO: 10) and #2032 (SEQ ID NO: 13) at 20 μM. The concentration of Taq polymerase was 2 fold over that used in previously stated reactions, but the concentrations of all other reaction components and the PCR method remained the same as in the production of Fragments A and B, described above. A toothpick was pricked into each clone, and then into the 25 μl PCR reaction mix to supply the template for the expected band of approximately 275 b.p., of which all clones were positive when run on 2% agarose gel stained with ethidium bromide.

Five hundred milliliter of 2× YT medium (ampicillin, 100 μg/ml) was inoculated from the patches of the first four clones (#1–4), and grown overnight to purify DNA using Qiagen maxi columns, using the manufacturer's standard protocol (DIAGEN GmbH). All four clones were positive for the appropriate insert by diagnostic digests with EcoRI and BamHI when run out on 2% agarose gel. The inserts of clones #1, #2, and #4 were confirmed by sequencing. Clone #1 was re-isolated from two 500 ml bacteria cultures inoculated from the patches (described above), as 4 batches using Qiagen Midi columns (DIAGEN GmbH).

EXAMPLE 3

Expression of Hirudin in *H. polymorpha* Using a Preprocollagen Signal Sequence

The pMPT121 expression vector containing the preprocollagen signal sequence-hirudin gene (referred to as Col- Hirudin) was introduced into *H. polymorpha* cells to allow for expression of hirudin in the *H. polymorpha* cells.

A. Transformation of Yeast Cells

To prepare competent yeast cells for transformation, three milliliters YPD MEDIUM (1.0% Yeast Extract, 2.0% Peptone, 2.0% Dextrose) was inoculated with 200 µl of an overnight culture of the methylotrophic yeast strain *Hansenula polymorpha* RB 11, a URA 3 auxotroph (Rhein Biotech; Düsseldorf, Germany; Roggenkamp, R. et al. (1986) *Mol. Gen. Genet.* 202:302–308). After overnight growth at 37° C., 700 µl of the culture was used to inoculate 200 ml YPD and grown for approximately 7 hours until $OD_{600}=0.9$.

Cells were spun at 2,000 rpm for 5 minutes at room temperature in a tabletop centrifuge, washed with 100 ml solution A (1M sorbitol, 10 mM Bicine pH 8.35, 3% ethyleneglycol (autoclaved)), spun again, and resuspended in 4 ml solution A. Two hundred twenty microliters of freshly thawed dimethylsulfoxide (DMSO) was added and mixed with the cell suspension and then dispensed in 200 µl aliquots. Aliquots were immediately frozen in liquid Nitrogen, and then stored at −80° C. for at least 16 hours before being used for transformation.

The transformation procedure was adapted from the protocol described in Dohmen, R. et al. (1991) *Yeast* 7:691–692. One hundred micrograms of expression plasmid Col-Hirudin clone #1 (prepared as described in Example 2) and 400 µg of herring sperm DNA (Sigma Chemical Co., St. Louis, Mo., D7290) as carrier was mixed. As a negative control, carrier DNA alone was used for a mock transformation. 18.5 µl of the above mix was then added to each of 10 frozen competent RB 11 aliquots. Tubes were agitated at 37° C. (Eppendorf Thermomixer 5436) for 5 minutes. Solution B(1.5 ml of 40% PEG 3350, 200 mM Bicine pH 8.35(filter sterilized)) was added to each tube, which was then incubated at 37° C. for 1 hour. Cells were then spun at 30% power in Sorvall Instrument (Dupont) Microspin 24S for 5 minutes. The cell pellet was then washed with 1.5 ml solution C(150 mM NaCl, 10 mM Bicine pH 8.35 (autoclaved)), spun again, and resuspended in 200 µl solution C.

Two 100 µl aliquots were plated, each on selective YNB plates (0.14% Yeast Nitrogen Base [without ammoniumsulfate], 0.5% ammoniumsulfate, 2.0% glucose, 2.0% agar). The negative control sample was plated, 100 µl on a selective plate, and 100 µl on a complete YPD plate (1% Yeast Extract, 2.0% Peptone, 2.0% Dextrose, 2.0% agar). Plates were inverted and incubated at 37° C. for 5 nights, at which point 334 colonies had developed. No colonies came up with the negative control on the selective plate, and an even lawn appeared on the nonselective YPD plate. One hundred colonies were identified, sized classified, and patched onto selective YNB 2% glucose plates and grown at 37° C. for two nights, at which time the plates were wrapped and saved at 4° C.

B. Passaging of Transformants for Integration of the Plasmid into Yeast Genome

Three milliliters of YNB (with 2% glucose) was inoculated with a small mass of forty (#s 1–40), of the patches above (=Pass #1). After 4 nights of incubation at 37° C. on a roller drum, the cultures were dense enough to begin Pass #2 with 50 µl into another 3 ml of YNB, 2% glucose. Growth and passaging continued at 37° C. on the roller as follows: 300 µl was used for Pass #3, and 100 µl was used when the cultures had grown fairly turbid for each of the following passes #4-#8. At pass #6 several clones were observed to be growing much slower than the rest, and were displaying a grainy or clumpy texture. These clones were allowed to grow longer to reach the same density, while the remainder were held at 4° C.

At Pass #9, 100 µl of culture was used to inoculate 3 ml of YNB (with 2% glycerol instead of glucose) to prepare cells for induction. Pass #10 was the same, and at this point, 500 µl of cells from Pass #9 were frozen down in 25% Glycerol at −80° C. When the cultures in Pass #10 looked reasonably turbid, 200 µl was used to inoculate 3 ml YNB (with 0.5% glycerol) to derepress the cells for expression testing (Gellissen, G. et al. (1992) *Biotech. Adv.* 10:179–189).

C. Expression Testing

Cultures #1–40 were grown under derepressive conditions, as described above, for 5 nights. At this point a random sample was taken to check density ($OD_{600}=3.39$). Methanol was added to each culture to a final concentration of 1%, and growth was continued overnight at 37° C., at which point the $OD_{600}=4.1$. To harvest the cultures, they were transferred into Falcon 2059 tubes and spun at 3,000 rpm for 15 minutes in a table top centrifuge. The supernatants were decanted into new tubes and stored at −80° C. until assays could be performed. Untransformed RB 11 was grown in semi-rich medium, supplemented with 0.5% glycerol and 0.02% uracil, and induced with 1% methanol in a similar method to be used as a negative control.

All forty of the induced culture supernatants and the negative control were tested for Hirudin activity in the supernatants using a thrombin inhibition assay. The decline in thrombin activity is determined photometrically using a chromogenic substrate for thrombin. A tri-peptide carrying p-nitroanaline (pNA) at the C-terminus (H-D-Phe-Pip-Arg-pNA, Sigma Chemical Co., No. S-2238) can have the pNA cleaved off by thrombin. This activity is inhibited by hirudin.

To test for hirudin activity in the supernatants, sample supernatants were diluted 1/10 in test buffer (10 mM Tris, 31 mM NaCl, 1% BSA, pH 8.0). One hundred microliters of each sample was applied to wells of a microtitre plate. Positive and negative controls contained 0.48 and 0.0 anti-thrombin units/ml, respectively, prepared from a standard hirudin solution. Twenty microliters of 2.5 NIH-U/ml human thrombin (Sigma Chemical Co., No. T-8885) was added to each well and incubated at 37° C. for 15 minutes. Fifty microliters of chromogenic substrate (0.83 mg/ml) was added to each well and incubation was carried out for an additional 2 minutes. The rate of substrate cleavage at 37° C. was determined at 10 second intervals over 2 minutes by measuring absorbence at 405 nm on a Molecular Devices Kinetic Plate Reader using Softmax software. Samples containing active hirudin were scored as having greater than 80% inhibition of thrombin activity. This assay was used as a plus/minus screening method only, and not for quantitation of actual expression levels. The assay was performed in duplicate with consistent results, showing 27 transformants positive for hirudin expression out of the forty total. It is important to note that these cultures represent mixed populations of transformants until stability passaging is complete.

D. Passaging Positive Expressors for Stability

To ensure that plasmid integration is stable and to increase the copy-number of plasmids within the chromosome of the expressing clones (Roggenkamp, R. et al. (1984) *Mol. Gen. Genet.* 194:489–493), transformant cultures are passaged through a series of selective and nonselective growth conditions in order to eliminate unstable plasmids from passaged culture. Three milliliters of YPD were inoculated with a heavy inoculum from the frozen seeds of the transformants shown to be positive by the Thrombin inhibition assay, described above (27 transformants in total), made at Pass//9. Cultures were grown to density (3 nights at 37° C.). This was designated Pass//S-1. Passages were performed as for integration described above, except that media was alternated between YNB 2% glucose and YPD, and only 25 µl was used as inoculum for each successive passage.

After Pass//S-5, cultures were plated out at $1.5 \times 10^{-8}$ on either selective or nonselective plates in order to compare numbers of cells retaining integrated plasmid versus those that may be losing the plasmid. In this process, single colonies are obtained representing true clones for further expression testing. Most paired platings had colony counts close enough to suggest that stability had been achieved (within 20% variation in most cases). Four clones designated A,B,C, and D, of each of the 10 most stable transformants were picked into 3 ml of semi-rich medium, 2% glycerol, for further expression testing on clone A of each of the 10 transformants (described below in subsection E).

To confirm the supposition that no gene rearrangement had occurred in the process of integration, and that the preprocollagen signal sequence was directing the Hirudin secretion from these cells, PCR screening was performed. PCR primers were designed to recognize regions in MOX-P (having the nucleotide sequence 5-GTC CCC ACA CGG TCC ATC TAT-3; SEQ ID NO: 14) and MOX-T (having the nucleotide sequence 5-GCG GTA TGT CCT TCC ACG TC-3; SEQ ID NO: 15) which span a region of about 100 b.p. over the uninterrupted polylinker site of the vector pMPT121. Insertion of the Col-hirudin nucleotide sequence would then yield a PCR product of just over 350 b.p. in length. PCR reactions and temperature cycling were set up as for Fragments A and B, described in Example 2, in 25 µl volumes, except that 0.5 µl of the primers shown in SEQ ID NO: 14 and 15, at 20 µM each were used, and a toothpick point touched to the patched cells was used as the source of template for the reaction. One nanogram of the Col-Hir #1 plasmid was used as template for a positive control under the same conditions. All tested clones produced PCR fragments corresponding to that of the Col-Hirudin #1 plasmid at approximately 385 b.p.

E. Expression from Individual Clones

After 3 nights of growth at 37° C. of clones of each transformant (described above), 500 µl of culture was frozen at -80° C. in 25% glycerol for use as seeds for later testing. Clones were reintroduced into culture by inoculating 3 ml YNB, with 2% glycerol, with a heavy inoculum and grown until dense (4 nights). Clonal cultures were then patched onto YPD plates for later PCR screening. 100 µl was used to inoculate a culture which was kept under derepressive conditions for 3 nights and then induced with methanol, as described above. At the time of harvesting, the average $OD_{600}$ of 4 randomly selected cultures was 1.72.

Upon Thrombin inhibition assaying of these clones, expression levels of clones derived from the same transformant, had comparable activity levels. All tested clones produced PCR fragments corresponding to that of the Col-Hirudin #1 plasmid at approximately 385 b.p.

For large scale growth and expression studies, six milliliters of overnight cultures in YNB, with 2% glycerol, of 7 of the best expressors (only 1 from each transformant), as ascertained from test thrombin inhibition assays, were used to inoculate 50 ml of 2×YNB, with 1.5% glycerol, in 125 ml Erlenmeyer flasks. The 50 ml cultures were grown at 37° C. at 200 rpm, and growth was monitored by frequent $OD_{600}$ readings. The initial O.D.s were all between 0.323 and 0.396. After 72 hours of growth, 5 cultures having entered plateau phase were harvested by a 15 minute spin at 4,800 rpm in a Sorvall RC5-B centrifuge. The remaining cultures were harvested in a similar manner 5 hours later. Supernatants from culture were passed through 0.2 µm filters, and then frozen at -20° C. PCR screening performed exactly the same as for the stables screening, described above, showed bands at the expected size of about 385 b.p.

Frozen supernatants were subjected to HPLC analysis, to detect the presence of Hirudin and its breakdown products in solution. This assay utilizes a reverse phase column to bind the proteins and then selectively elute them separating the different species. The proteins are also quantitated by the use of a standard curve made from correlating the area under the peaks to total protein injected. Specific parameters of the assay are listed below.

Column: Vydac C8 (4.6mm ID×25 cm L, Rainin Cat. #208-TP546) (5 µm packing, 330 Ao pore size)

| Buffers: | A: | 250 mM Sodium Perchlorate |
| | | 0.1% Trifluoroacetic Acid |
| | B: | 80% Acetonitrile/water |
| | | 0.1% Trifluoroacetic Acid |

Flow Rate: 1.5 ml/min
Detection: 216 nm

The assay was run at 30° C. using a column oven. The column was equilibrated in 100% Buffer A and the following gradient was applied to elute the proteins.

| Time | Event | Value |
| --- | --- | --- |
| 0.5 | B.Conc | 0.0 |
| 3.0 | B.Conc | 25.0 |
| 19.07 | B.Conc | 34.0 |

The culture sample (undiluted) was injected into the column and the column was washed in 100% Buffer A for 0.5 minutes. Then, a gradient from 0%–25% Buffer B was run to wash off contaminants. Hirudin and its breakdown products were then eluted with a gradient from 25%–34% Buffer B. Retention time of Hirudin H65 was 17.2 min.

The results of the HPLC analysis of the supernatants of seven clones are shown below.

| Clone I.D. | OD 600 nm at Harvest | µg/ml of correctly processed Hirudin |
| --- | --- | --- |
| 1B | 13.0 | 1.97 |
| 5A | 16.7 | 1.67 |
| 6A | 13.9 | 3.20 |
| 7C | 15.1 | 2.85 |
| 8A | 15.3 | 1.20 |
| 10A | 14.2 | 0.60 |
| 16A | 16.1 | 1.27 |

These results demonstrate that a hirudin gene expressed from a preprocollagen signal sequence in *H. polymorpha* leads to production of hirudin protein in the cells which can be detected and recovered from the culture medium.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. An isolated nucleic acid molecule comprising a first nucleotide sequence encoding a preprocollagen signal sequence operatively linked to a second nucleotide sequence encoding a heterologous protein of interest.

2. The nucleic acid of claim 1, wherein the preprocollagen signal sequence is mammalian.

3. The nucleic acid of claim 2, wherein the preprocollagen signal sequence is human.

4. The nucleic acid of claim 1, wherein the preprocollagen signal sequence is a Type I preprocollagen signal sequence.

5. The nucleic acid of claim 4, wherein the preprocollagen signal sequence comprises the amino acid sequence shown in SEQ ID NO: 1.

6. The nucleic acid of claim 5, wherein the preprocollagen signal sequence comprises the amino acid sequence shown in SEQ ID NO: 2.

7. The nucleic acid of claim 1, which is DNA.

8. A recombinant expression vector comprising a first DNA sequence encoding a preprocollagen signal sequence operatively linked to a second DNA sequence encoding a heterologous protein of interest.

9. The vector of claim 8, which is suitable for expression of the protein of interest in a yeast cell.

10. The vector of claim 9, wherein the yeast cell is a *Hansenula polymorpha* cell.

11. The vector of claim 8, which is suitable for expression of the protein of interest in a mammalian cell.

12. The vector of claim 8, wherein the preprocollagen signal sequence is mammalian.

13. The vector of claim 12, wherein the preprocollagen signal sequence is human.

14. The vector of claim 8, wherein the preprocollagen signal sequence is a Type I preprocollagen signal sequence.

15. The vector of claim 14, wherein the preprocollagen signal sequence comprises the amino acid sequence shown in SEQ ID NO: 1.

16. The vector of claim 15, wherein the preprocollagen signal sequence comprises the amino acid sequence shown in SEQ ID NO: 2.

17. The vector of claim 8, wherein the protein of interest is hirudin.

18. A eukaryotic host cell containing a recombinant expression vector comprising a first DNA sequence encoding a preprocollagen signal sequence operatively linked to a second DNA sequence encoding a heterologous protein of interest.

19. The eukaryotic host cell of claim 18, which is a yeast cell.

20. The eukaryotic host cell of claim 19, which is a *Hansenula polymorpha* cell.

21. The eukaryotic host cell of claim 18, which is a mammalian cell.

22. The eukaryotic host cell of claim 18, wherein the preprocollagen signal sequence is mammalian.

23. The eukaryotic host cell of claim 22, wherein the preprocollagen signal sequence is human.

24. The eukaryotic host cell of claim 18, wherein the preprocollagen signal sequence is a Type I preprocollagen signal sequence.

25. The eukaryotic host cell of claim 24, wherein the preprocollagen signal sequence comprises the amino acid sequence shown in SEQ ID NO: 1.

26. The eukaryotic host cell of claim 25, wherein the preprocollagen signal sequence comprises the amino acid sequence shown in SEQ ID NO: 2.

27. The eukaryotic host cell of claim 18, wherein the protein of interest is hirudin.

28. A method for producing a protein of interest, comprising culturing a eukaryotic host cell containing a recombinant expression vector comprising a first DNA sequence encoding a preprocollagen signal sequence operatively linked to a second DNA sequence encoding a heterologous protein of interest such that the heterologous protein of interest is produced by the host cell.

29. The method of claim 28, wherein the protein of interest is secreted by the eukaryotic host cell into a culture medium.

30. The method of claim 29, further comprising recovering the protein of interest from the culture medium.

31. The method of claim 28, wherein the eukaryotic host cell is a yeast cell.

32. The method of claim 31, wherein the eukaryotic host cell is a *Hansenula polymorpha* cell.

33. The method of claim 28, wherein the eukaryotic host cell is a mammalian cell.

34. The method of claim 28, wherein the preprocollagen signal sequence is mammalian.

35. The method of claim 34, wherein the preprocollagen signal sequence is human.

36. The method of claim 28, wherein the preprocollagen signal sequence is a Type I preprocollagen signal sequence.

37. The method of claim 36, wherein the preprocollagen signal sequence comprises the amino acid sequence shown in SEQ ID NO: 1.

38. The method of claim 37, wherein the preprocollagen signal sequence comprises the amino acid sequence shown in SEQ ID NO: 2.

39. The method of claim 28, wherein the protein of interest is hirudin.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 2
        ( D ) OTHER INFORMATION: /note="Xaa is Phe or Leu"

( i x ) FEATURE:
        ( A ) NAME/KEY: Modified-site
        ( B ) LOCATION: 7
        ( D ) OTHER INFORMATION: /note="Xaa is Leu, Ser or Thr"

( i x ) FEATURE:
        ( A ) NAME/KEY: Modified-site
        ( B ) LOCATION: 9
        ( D ) OTHER INFORMATION: /note="Xaa is Leu, Ile or Thr"

( i x ) FEATURE:
        ( A ) NAME/KEY: Modified-site
        ( B ) LOCATION: 13
        ( D ) OTHER INFORMATION: /note="Xaa is Leu or Ile"

( i x ) FEATURE:
        ( A ) NAME/KEY: Modified-site
        ( B ) LOCATION: 15
        ( D ) OTHER INFORMATION: /note="Xaa is Ala or Val"

( i x ) FEATURE:
        ( A ) NAME/KEY: Modified-site
        ( B ) LOCATION: 17
        ( D ) OTHER INFORMATION: /note="Xaa is Ala, Val, Ser or Leu"

( i x ) FEATURE:
        ( A ) NAME/KEY: Modified-site
        ( B ) LOCATION: 18
        ( D ) OTHER INFORMATION: /note="Xaa is Leu, Tyr or Cys"

( i x ) FEATURE:
        ( A ) NAME/KEY: Modified-site
        ( B ) LOCATION: 20
        ( D ) OTHER INFORMATION: /note="Xaa is Thr or Ala"

( i x ) FEATURE:
        ( A ) NAME/KEY: Modified-site
        ( B ) LOCATION: 21
        ( D ) OTHER INFORMATION: /note="Xaa is His, Arg or Thr"

( i x ) FEATURE:
        ( A ) NAME/KEY: Modified-site
        ( B ) LOCATION: 22
        ( D ) OTHER INFORMATION: /note="Xaa is Gly, Cys or Ser"

( x i ) SEQUENCE DESCRIPTION: SEQ ID NO:1:

```
       Met Xaa Ser Phe Val Asp Xaa Arg Xaa Leu Leu Leu Xaa Ala Xaa Thr
       1               5                   10                  15

Xaa Xaa Leu Xaa Xaa Xaa
                   20
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
       Met Phe Ser Phe Val Asp Leu Arg Leu Leu Leu Leu Ala Ala Thr
       1               5                   10                  15

Ala Leu Leu Thr His Gly
                   20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 17
        ( D ) OTHER INFORMATION: /note="Xaa is Val or Ile"

( x i ) SEQUENCE DESCRIPTION: SEQ ID NO:3:

```
       Met Ile Arg Leu Gly Ala Pro Gln Ser Leu Val Leu Leu Thr Leu Leu
       1               5                   10                  15

Xaa Ala Ala Val Leu Arg Cys
                   20
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 7
        ( D ) OTHER INFORMATION: /note="Xaa is Lys or Ser"

( i x ) FEATURE:
        ( A ) NAME/KEY: Modified-site
        ( B ) LOCATION: 8
        ( D ) OTHER INFORMATION: /note="Xaa is Gly or Val"

( i x ) FEATURE:
        ( A ) NAME/KEY: Modified-site
        ( B ) LOCATION: 9
        ( D ) OTHER INFORMATION: /note="Xaa is Ser or Thr"

( i x ) FEATURE:
        ( A ) NAME/KEY: Modified-site (B) LOCATION: 10
(D) OTHER INFORMATION: /note="Xaa is Trp or Leu"

(ix) FEATURE:
(A) NAME/KEY: Modified-site
(B) LOCATION: 11
(D) OTHER INFORMATION: /note="Xaa is Leu or Phe"

(ix) FEATURE:
(A) NAME/KEY: Modified-site
(B) LOCATION: 12
(D) OTHER INFORMATION: /note="Xaa is Leu or Ile"

(ix) FEATURE:
(A) NAME/KEY: Modified-site
(B) LOCATION: 14
(D) OTHER INFORMATION: /note="Xaa is Ala or Thr"

(ix) FEATURE:
(A) NAME/KEY: Modified-site
(B) LOCATION: 15
(D) OTHER INFORMATION: /note="Xaa is Leu or Val"

(ix) FEATURE:
(A) NAME/KEY: Modified-site
(B) LOCATION: 16
(D) OTHER INFORMATION: /note="Xaa is Leu or Phe"

(ix) FEATURE:
(A) NAME/KEY: Modified-site
(B) LOCATION: 17
(D) OTHER INFORMATION: /note="Xaa is His or Gln"

(ix) FEATURE:
(A) NAME/KEY: Modified-site
(B) LOCATION: 19
(D) OTHER INFORMATION: /note="Xaa is Thr or Ser"

(ix) FEATURE:
(A) NAME/KEY: Modified-site
(B) LOCATION: 20
(D) OTHER INFORMATION: /note="Xaa is Ile, Val or Leu"

(xi) SEQUENCE DESCRIPTION: SEQ ID NO:4:

Met Met Ser Phe Val Gln Xaa Xaa Xaa Xaa Xaa Xaa Leu Xaa Xaa Xaa
1               5                           10                          15

Xaa Pro Xaa Xaa Ile Leu Ala Gln
            20

(2) INFORMATION FOR SEQ ID NO:5:

(i) SEQUENCE CHARACTERISTICS:
(A) LENGTH: 18 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Modified-site
(B) LOCATION: 5
(D) OTHER INFORMATION: /note="Xaa is Ile or Thr"

(ix) FEATURE:
(A) NAME/KEY: Modified-site
(B) LOCATION: 6
(D) OTHER INFORMATION: /note="Xaa is Pro, Ala or Ser"

(ix) FEATURE:
(A) NAME/KEY: Modified-site
(B) LOCATION: 7
(D) OTHER INFORMATION: /note="Xaa is Pro or Leu"

(ix) FEATURE:
(A) NAME/KEY: Modified-site ( B ) LOCATION: 11
                    ( D ) OTHER INFORMATION: /note="Xaa is Met or Phe"

( i x ) FEATURE:
                    ( A ) NAME/KEY: Modified-site
                    ( B ) LOCATION: 12
                    ( D ) OTHER INFORMATION: /note="Xaa is Phe, Ser or Cys"

( i x ) FEATURE:
                    ( A ) NAME/KEY: Modified-site
                    ( B ) LOCATION: 14
                    ( D ) OTHER INFORMATION: /note="Xaa is Thr or Asn"

( i x ) FEATURE:
                    ( A ) NAME/KEY: Modified-site
                    ( B ) LOCATION: 15
                    ( D ) OTHER INFORMATION: /note="Xaa is Leu or Ile"

( x i ) SEQUENCE DESCRIPTION: SEQ ID NO:5:

Met  Leu  Pro  Gln  Xaa  Xaa  Xaa  Leu  Leu  Leu  Xaa  Xaa  Asp  Xaa  Xaa  Val
 1                    5                              10                             15

His  Gly ( 2 ) INFORMATION FOR SEQ ID NO:6:

( i ) SEQUENCE CHARACTERISTICS:
                    ( A ) LENGTH: 23 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:6:

Met  Leu  Pro  Phe  Trp  Lys  Arg  Leu  Leu  Tyr  Ala  Ala  Val  Ile  Ala  Gly
 1                    5                              10                             15

Ala  Leu  Val  Gly  Ala  Asp  Ala
                20

( 2 ) INFORMATION FOR SEQ ID NO:7:

( i ) SEQUENCE CHARACTERISTICS:
                    ( A ) LENGTH: 26 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:7:

Met  Lys  Gln  Arg  Ala  Ala  Leu  Gly  Pro  Val  Leu  Arg  Leu  Ala  Ile  Leu
 1                    5                              10                             15

Ala  Leu  Leu  Ala  Val  Ser  Tyr  Val  Gln  Ser
                20                         25

( 2 ) INFORMATION FOR SEQ ID NO:8:

( i ) SEQUENCE CHARACTERISTICS:
                    ( A ) LENGTH: 14 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:8:

Pro  Pro  Gly  Pro  Pro  Gly  Pro  Pro  Gly  Pro  Pro  Gly  Pro  Pro ( 2 ) INFORMATION FOR SEQ ID NO:9:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

Gly Pro Pro Gly Pro Pro Gly Pro Pro Gly Pro Pro Gly
1               5                   10

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:10:

TTTTGAATTC ATGTTCTCCT TCGTC                                            25

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:11:

GTGCAGTCAG TGTAAACAAC GCCGTGGGTC AGCAGCGC                        38

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:12:

GCGCTGCTGA CCCACGGCGT TGTTTACACT GACTGC                            36

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:13:

GGGGGATCCC TATTACTGCA GGTATTCTTC CGGG                              34

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:14:

GTCCCCACAC GGTCCATCTA T 21

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:15:

GCGGTATGTC CTTCCACGTC 20